United States Patent [19]

Sjölinder

[11] 4,379,450

[45] Apr. 12, 1983

[54] TRACTION BENCHES

[76] Inventor: Per-Olof Sjölinder, Tanneforsgatan 3, S-582 24 Linköping, Sweden

[21] Appl. No.: 217,499

[22] Filed: Dec. 17, 1980

[51] Int. Cl.[3] .................... A61F 5/00

[52] U.S. Cl. .................... 128/74

[58] Field of Search .................... 128/69, 71–75

[56] References Cited

U.S. PATENT DOCUMENTS

| | | | |
|---|---|---|---|
| 1,351,482 | 8/1920 | McManis | 128/74 |
| 1,371,502 | 3/1921 | McManis | 128/74 |
| 1,390,301 | 9/1921 | McManis | 128/74 |
| 1,661,491 | 3/1928 | Minty . | |
| 4,002,165 | 1/1977 | Lind . | |

FOREIGN PATENT DOCUMENTS

| | | |
|---|---|---|
| 2357236 | 1/1978 | France . |
| 334977 | 5/1971 | Sweden . |
| 360560 | 8/1973 | Sweden . |
| 7406049-2 | 4/1977 | Sweden . |
| 7614728-9 | 12/1978 | Sweden . |

*Primary Examiner*—Richard J. Apley
*Attorney, Agent, or Firm*—Pollock, Vande Sande & Priddy

[57] ABSTRACT

A traction bench for treatment of the vertebral column and extremities of the human body comprises a table-like support on which a patient to be treated lies, the support being mounted on a pedestal base with a table support frame and including at least two longitudinally aligned table top sections. At least one of the table top sections, and preferably both, is journalled in the frame for free sliding motion longitudinally of the traction bench, fixation means for securing the patient to the traction bench and the table top sections and their associated frames are also so mounted that they may be displaced laterally relative to one another, and so that each section may also be tilted selectively about a first axis extending transversely of the bench and about a second axis extending longitudinally of the bench. The bench also includes and further includes power traction means of the hydraulic cylinder type for applying a traction force to the patient. The fixation means includes a rod member which is connected to a harness adapted to be applied around the trunk or extremities of the patient and longitudinally adjustably mounted on a retainer bar which is adapted to be secured at substantially freely selectable locations on said table top sections.

5 Claims, 12 Drawing Figures

TRACTION BENCHES

Figure 1:
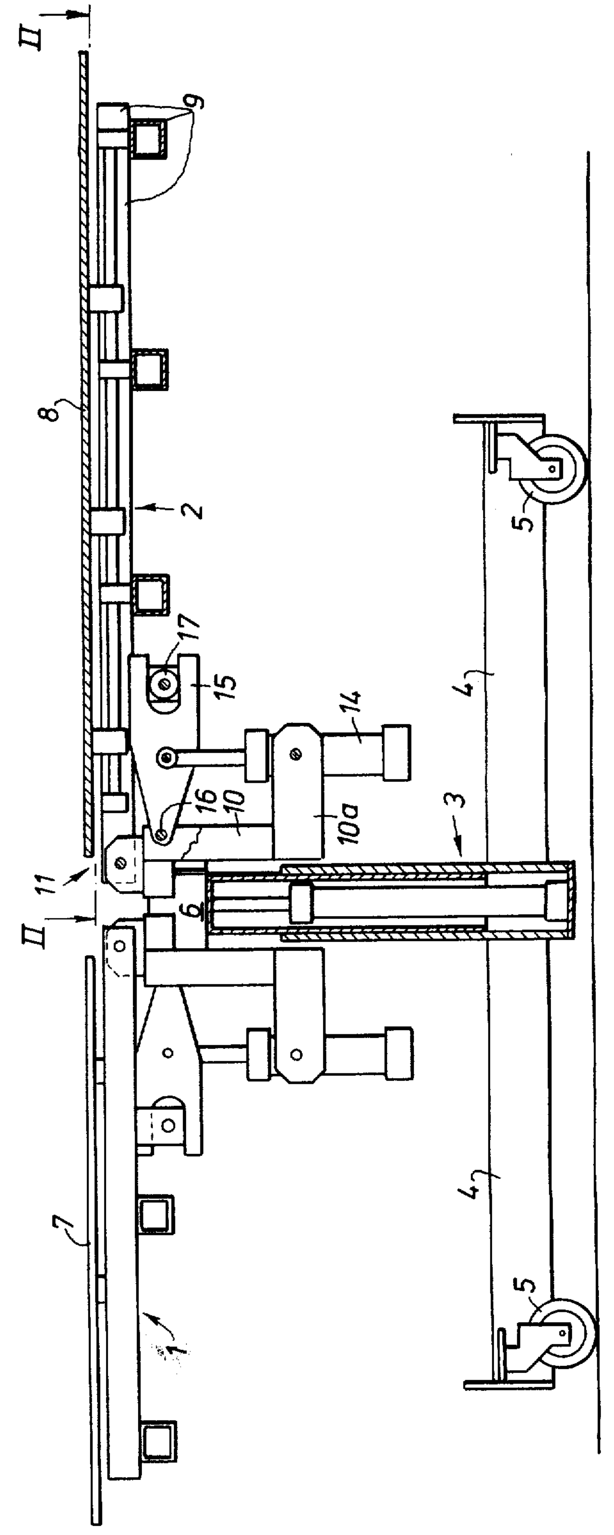

The present invention relates to a traction bench for traction treatment of vertebral column and extremities of the human body and comprising (i) a table-like support, on which a patient to be treated lies, mounted on a floor-supported base of the central pedestal type, said table-like support including at least two longitudinally aligned table top sections, at least one of which is journalled in an associated support frame for free sliding motion longitudinally of the bench, at least the portion of the frame supporting one of the table top sections furthermore being pivotable about a substantially horizontal transverse axis in the boundary area between the table top sections by means of an adjustment element of hydraulic cylinder type, (ii) fixation means for securing the patient to the traction bench with the portion of the body, to which the traction treatment is to be applied, being located substantially adjacent the boundary area between the table top sections, and (iii) power traction means of the hydraulic cylinder type for applying a traction force to the patient.

Traction benches are already known in a number of various embodiments. Common to them all is that they are adapted almost exclusively for carrying out one or a pair of specific treatments of some specific portion of the human body. For example, Lind U.S. Pat. No. 4,002,165, issued Jan. 11, 1977, for "Auto-Traction Table" discloses a traction bench which is power adjustable and more closely mechanically adjustable to an initial position and to which the patient is secured by means of a harness which is anchored to a frame-work at one end of the bench. The traction action is provided, however, by the patient himself who seizes a framework at the opposite end of the bench according to the principle of so-called autotraction. This type of bench is designed with particular regard to the treatment of the spinal or vertebral column but is not suited for other treatments of e.g. extremities. Such a bench also exhibits other substantial disadvantages, e.g., the friction which occurs between the surface of the patient support and the body of the patient. Said friction many times tends to be intermittently varying and may be a so-called "stick-slip" phenomenon but it might also occur that the friction varies with time, such as during lengthy treatments when the patient perspires and the coefficient of friction at the contact surface varies.

A technically much more advanced bench is disclosed in Swedish patent specification No. 360,560. In order to eliminate the last-mentioned "stick-slip" phenomenon one of the patient support portions is made freely slideable longitudinally relative to the other support portion. However this bench is also almost exclusively adapted for treatment of the vertebral column, and is not suited for extremity treatments.

A similar bench is described in Swedish lay-open print 7614728-9, this bench also being adapted solely for vertebral column traction.

The procedure of applying traction to the vertebral column and the extremities is becoming more widespread and therefore there is an obvious need for a much more universally usable form of traction bench which will provide for several different kinds of treatment of the vertebral column as well as of extremities. From a general point of view the forces required for the traction can either be applied by the patient himself or by another person, e.g., a doctor or physical therapist. In the latter case the therapist might use his own muscle power for providing directly the required forces to the patient or he could utilize power amplifiers or external power sources.

The object of the present invention is to provide a traction bench which is universally usable and lacks the drawbacks of prior benches. This object is achieved according to the present invention by providing a traction bench wherein at least one of the table top sections is journalled for free sliding motion as a whole in both a longitudinal and in a transverse direction on a table support frame the table top section also being tiltable about either or both of two transverse axes, and fixation means are provided which includes a rod member that is connected with a harness known per se and adapted to be applied around the trunk or extremities of the patient and which is longitudinally adjustably mounted on a retainer bar, which is adapted to be securely mounted at substantially freely selectable locations on said table top sections, padding on said table top sections, if any, being provided with recesses for accomodation of said rod member and retainer bar, the hydraulic cylinder power tractions means acting between the table support frame and at least one of the table top sections and being easily releasably connected to the table top section.

A further object of the invention is to provide a traction bench in which the various body portions of the patient rest on the two table top sections of the patient support. As a result, e.g. when subjecting a leg to traction, the trunk of the patient can rest on and be secured to one of the table top sections while the leg to be treated can be secured to the other table top section. By this arrangement, the leg to be treated is supported along its entire length so that its own weight has no adverse effect on the force action during the treatment, which otherwise would be the case if the leg were to be raised from the support and secured in an elevated position to a member such as a clamp at the foot end of the bench. Another object of the invention is to improve the bench so as to provide for the carrying out of all the three aforementioned kinds of traction treatment, namely by means of traction forces developed by the patient himself or by means of traction forces developed by a therapist using his own muscle power or some form of power assistance or an external power source.

An important additional advantage of the present invention is that the design of the bench also allows the carrying out of an entirely novel specific examination and treatment procedure, namely a determination of changes of the mobility, under-mobility as well as over-mobility, between each pair of vertebrae of the vertebral column such as will be further explained in the following description.

Figure 3:
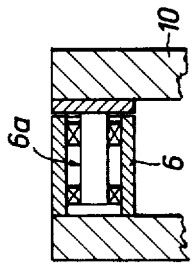
Figure 2:
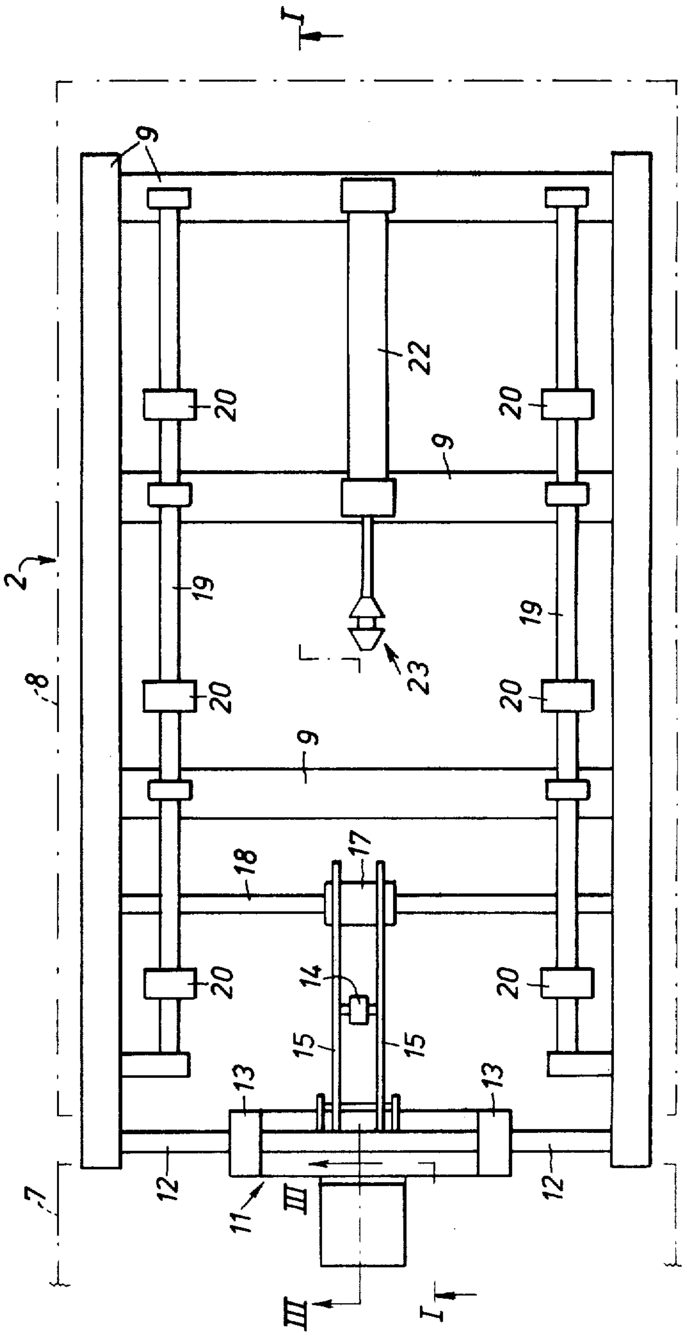
Figure 4:
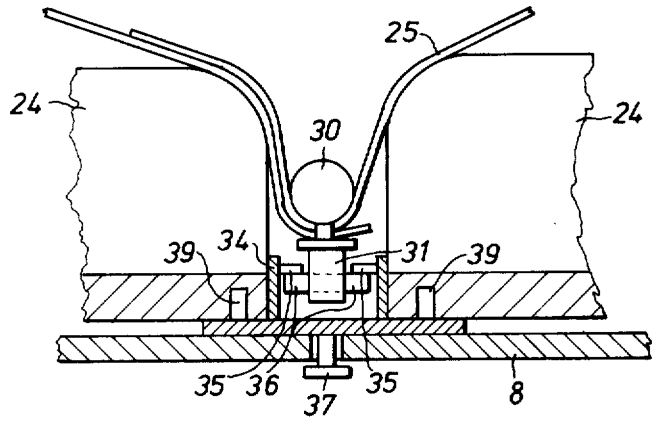
Figure 5:
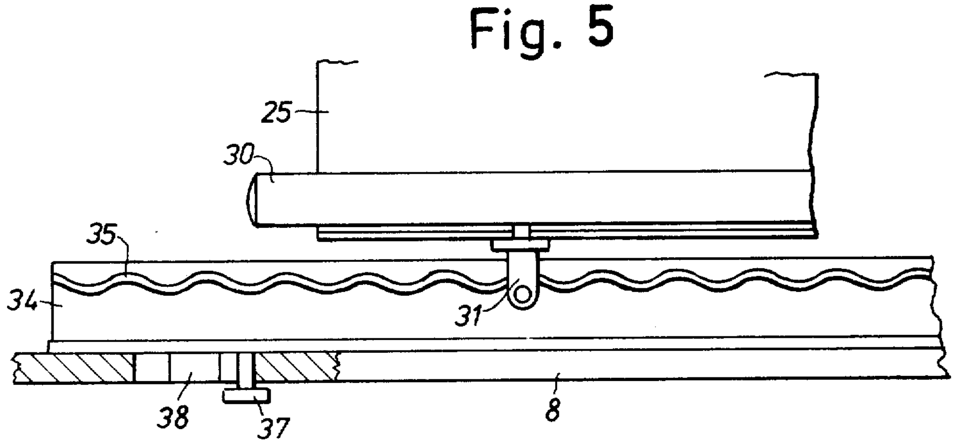
Figure 7:
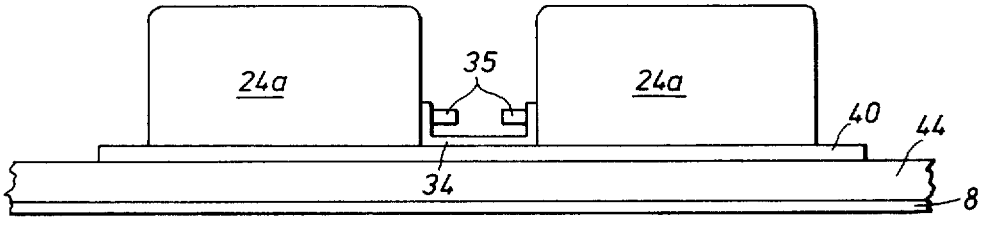
Figure 6:
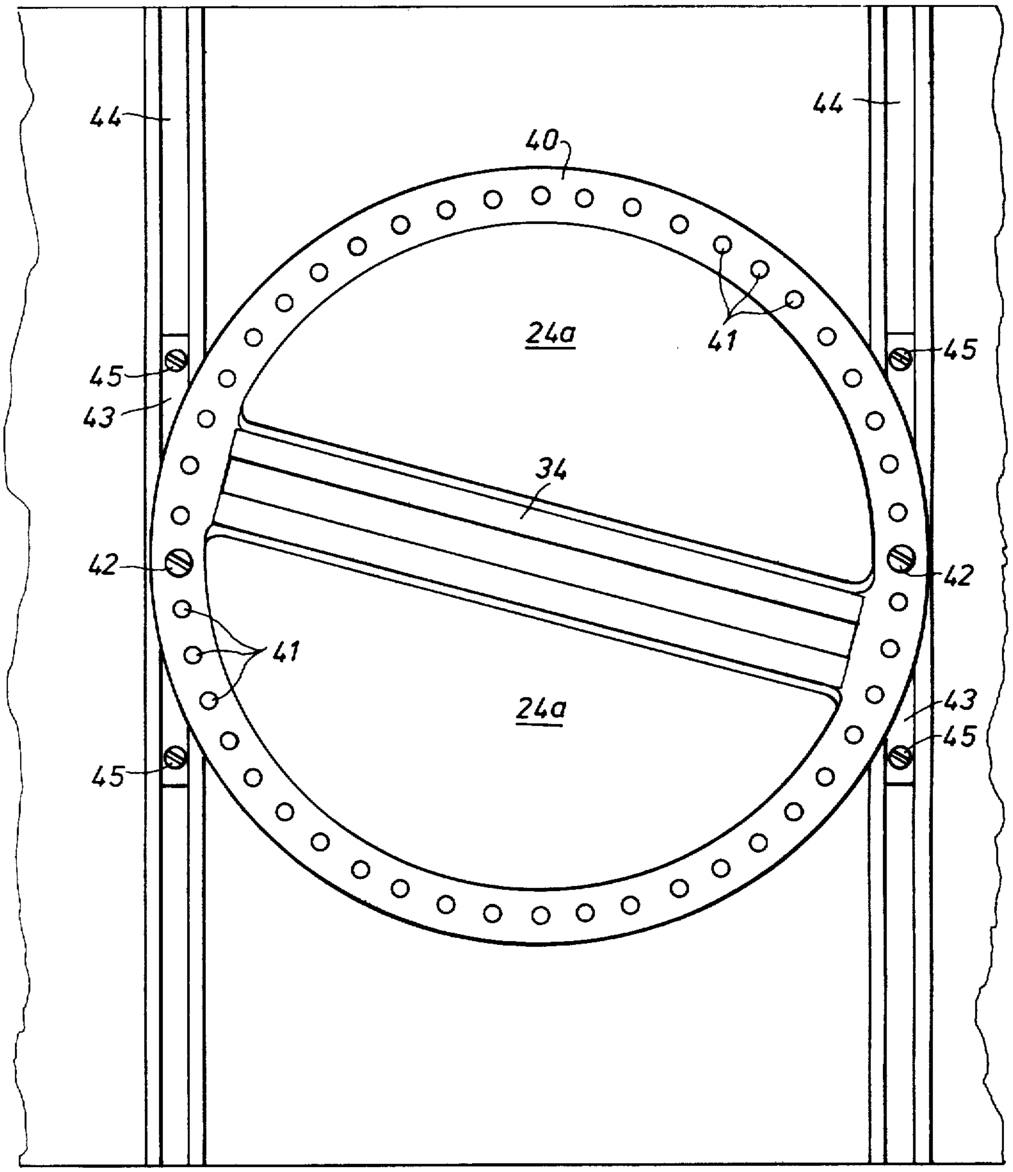
Figure 8A:
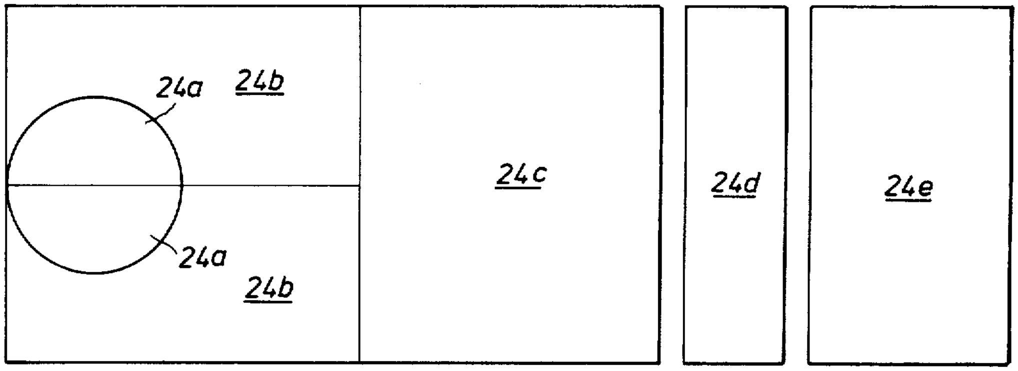
Figure 8B:
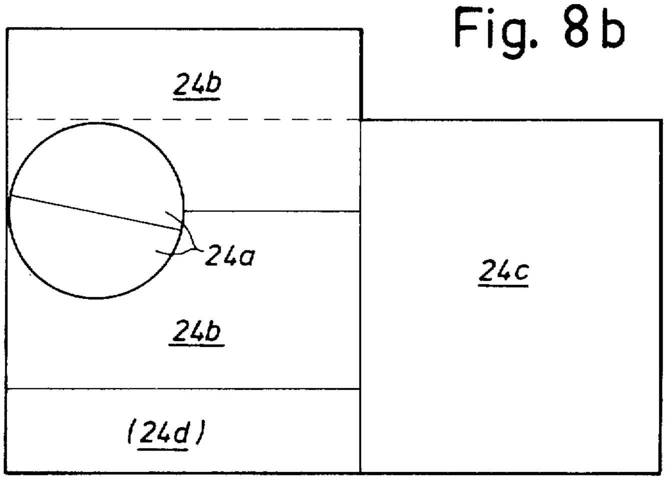
Figure 8C:
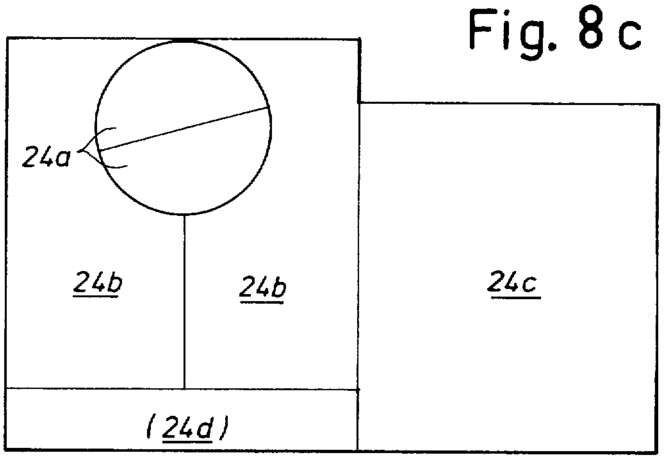
Figure 8D:
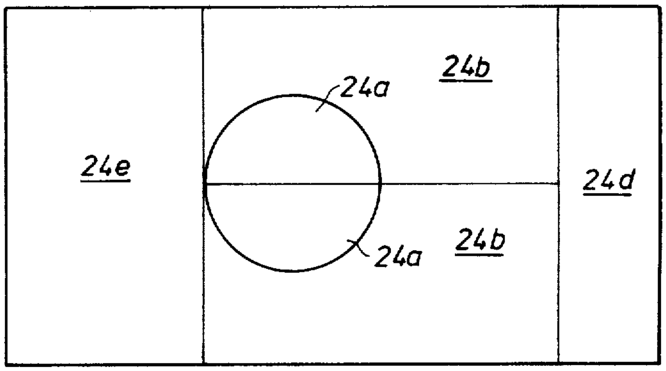
Figure 8E:
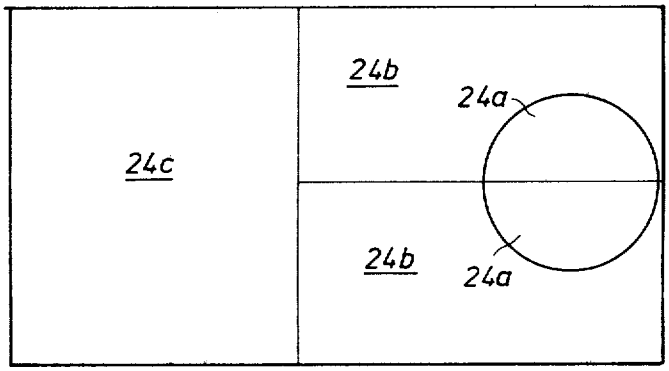

By way of example, the invention will be further described below with reference to the accompanying drawings, in which FIG. 1 discloses a partly cross-sectional side elevational view of a traction bench according to the invention, FIG. 2 is a fragmentary plan view from above of the right hand portion of the table support frame of the bench illustrated in FIG. 1, FIG. 3 is a detail cross-sectional view through a pivot journal of said right hand table support frame portion taken along the line III—III in FIG. 2, FIGS. 4 and 5 are an end view and a side elevational view, respectively, of an embodiment of the fixation means, FIG. 6 is a plan view from above and FIG. 7 is another end view of the illustrated embodiment of the fixation means, and FIGS. 8a–e are diagrammatic plan views of various alternative uses of said fixation means.

With reference to the drawings and particularly FIGS. 1 and 2 the traction bench according to the invention comprises a table-like support on which a patient to be treated lies, said support primarily being mounted on a table support frame 1, 2. Said support frame 1, 2 is in turn carried by a floor-supported base, which preferably is of the type including a central pedestal 3 so as to impose the smallest possible obstacle to the work of the therapist. Said pedestal 3 is supported on the floor by means of a frame 4, suitably equipped with wheels, such as castor wheels 5. In its upper end, the pedestal 3 is provided with a bearing head 6 carrying the movable portions of the traction bench.

As known per se the table-like support is divided at the middle of its length and therefore consists of two longitudinally aligned table top sections 7, 8, each supported by a portion 1, 2 of the table support frame. Each portion 1, 2 of said support frame preferably is made as a rectangular frame of tubes 9, preferably of square cross-section. In principle only one of the table top sections such as 8 needs to be movable with its support frame portion 2, but the drawings illustrate the preferred embodiment of the present invention in which the table top section 7 with associated support frame portion 1 is also movable in the same manner as section 8 relative the central pedestal 3. Since the movable units 7, 1 and 8, 2 are arranged in exactly the same way it will suffice to describe move specifically only the table top section 8 and its associated support frame portion 2, i.e., the portion of the traction bench located to the right of the central pedestal 3 as seen in FIGS. 1 and 2 of the drawings.

On the bearing head 6 of the unit in which the table top section 8 is included, there is mounted a bearing bracket 10 which is journalled in a bearing 6a so as to pivotable about an axis parallel to and somewhat below the longitudinal center axis of the table top sections 7 and 8. Hence the table top section 8 can be brought to incline transversely to a suitable extent and said inclining motion is provided by means of any suitable mechanism, not disclosed in the drawings, such as a screw-type mechanism.

At the upper end of said bearing bracket 10 is furthermore mounted a bearing unit 11 for a transverse shaft 12, secured to the end of the support frame portion 2 closest to the bearing head 6. Preferably said bearing unit 11 comprises a pair of mutually spaced bearings 13 which advantageously are made as ball bushings. Said ball bushings provide not only for a pivotable mounting of the shaft 12 so as to make the support frame portion 2 pivotable upwardly and downwardly around said shaft 12 with reference to the position illustrated in FIG. 1, but also provide for an axially reciprocating sliding motion, if desired. For providing the pivotal motion of the table top section 8 upwardly and downwardly the bearing bracket 10 also carries a suitable adjustment means 14, preferably an hydraulic cylinder. In the arrangement shown in the drawings, the hydraulic cylinder 14 is pivotally supported from an arm 10a extending from the bearing bracket 10, while the free end of the associated piston rod is pivotally connected to a yoke member 15 at an intermediary position thereof. At one of its ends said yoke member 15 is pivotally mounted by a bearing 16 to the bearing bracket 10, while said yoke member 15 at its other end has a yoke portion accomodating a bearing 17, preferably also a ball bushing. In said bearing 17 is slideably mounted a further transverse shaft or rod 18 which, together with the previously mentioned transverse shaft or rod 12 and the bearings 13 mounted thereon, provide for the sliding movements of the support frame portion 2 in a transverse direction.

Also arranged in the support frame portion 2 is a pair of longitudinal parallel bearing rods 19 on which bearings 20, preferably also made as ball bushings, are slideable, said bearings 20 being secured to the bottom surface of the table top section 8. By means of said bearings 20 the table top section 8 thus is movable longitudinally in opposing directions relative to the support frame section 2. With the previously described movability of the support frame portion 2 in a transverse direction said table top section 8 hence is freely movable in directions at right angles to each other parallel to its own plane. If the table top section to be locked against motion in one and/or the other direction of movement, said locking action can be provided by means of any known and suitable locking mechanism, such as one of the eccentric type.

While the free movability of the table top section 8 is adapted to be utilized when a therapist or the patient himself is to be responsible for the development of traction forces, it might be required on certain occasions to have some kind of mechanical and preferably hydraulic power amplification of the traction force and this can be provided by means of a hydraulic cylinder 22 mounted in the support frame portion 2. Said cylinder 22 preferably is double-acting and adapted to be actuated by a particular but not illustrated control means. At the free end of the associated piston rod the cylinder 22 is adapted to be connected with the table top section 8 by means of any coupling 23 of easy releasable kind, such as a remote-controlled locking hook or the like.

With the structural design of the bench now described at least the table top section 8, and also the table top section 7 when it is journalled in the same manner, is universally movable in space such as in no prior traction bench. In order to achieve a full utilization of all the possibilities of said traction bench to effective treatments of the patient, it is required, however, that the patient be fixed or secured to the bench, and particularly to the table top sections, in a different and more effective way than in benches hitherto known, and therefore the present invention also provides such an improved fixation.

The table top sections 7 and 8 constituting the support for the patient to be treated are of course provided on their upper surface with a padded cover or a cushion 24, divided into several portions if desired.

For securing the patient, prior art traction benches have included harnesses of various kinds. All of them fail, however, to provide a securing of the patient to the table top sections of the bench with sufficient rigidity to allow an effective traction application when the bench is universally adjustable to the great extent which characterizes the present invention. Particularly the padding on the table top sections 7, 8 tend to cause significant drawbacks and insufficient securing rigidity unless particular steps are taken as now will be suggested according to the present invention.

The basic concept of this connection is that the harness 25 (see FIGS. 4 and 5) is to be tensioned against the table top sections 7, 8 without any padding 24 intervening, so as to provide a really rigid fixation of the patient. This can be achieved by connecting the harness 25 in a suitable way to a rod 30 located thereunder. In said rod 30 are threaded hook means 31 which not only secure the harness 25 to said rod 30 but also provide for an engagement of rod 30 with a bar 34 which, in turn, is adjustably mounted on the table top sections 7, 8. Although the bar 34 might be shaped in many various ways it has been illustrated in the drawings as being substantially U-shape in cross-section, the upper inwardly directed flanges 35 thereof having a longitudinal wave form. The hook means 31 is equipped with laterally protruding studs 36 which engage below the flanges 35 and thus are prevented from being moved longitudinally of the bar 34 when a patient is secured in the harness 25. At the same time this design of the bar 34 with its wave-formed flanges 35 allows an easy change of the position of the bar 30 when the harness 25 is open or released.

The bar 34 is arranged so that it can be moved over, and affixed at any desired position on, the surface of the table top sections 7, 8 in any suitable way, e.g. the bottom surface of bar 34 can be provided with a plurality of studs 37 having heads that are adapted to be inserted into holes 38 which are of key-hole contour and equally spaced from one another over the surfaces of the table top sections 7, 8. The use of such a fixation of the harness 25 by means of a rod 30 and a securing bar 34 of course causes certain difficulties as far as the arrangement of the padding 24 on the table top sections 7, 8 is concerned. It is obvious, however, that such pads 24 are required in the present traction bench since otherwise the patient will be clamped against the rod 30 in an uncomfortable way. As is evident from FIG. 4 of the drawings it is therefore suitable to provide the table top sections 7, 8 with padding or individual pads 24 formed in suitable portions. The most essential thing in this connection is however that the different portions of the padding 24 should be located very closely adjacent to the opposing edges of the bar 34 and furthermore should have a height which, when load is applied, will secure a required clearance between the patient in the harness 25 and the rod 30. Although the key-hole-shaped apertures 38 in the table top sections 7, 8 also can be used for mounting the padding portions 24 at required positions, the drawings illustrate an alternative embodiment in which the pads 24 are kept located along the longitudinal edges of the bar 34 by means of pins 39 that extend upwardly from laterally protruding bottom flanges of the bar 34, said pins 39 being insertable in corresponding holes in the pads 24.

FIGS. 6–8 of the drawings disclose a further development of this embodiment of the fixation means, providing for effective use of a limited number of such padding portions.

The bar 34 is adapted to be mounted on a circular disk 40 provided with equally spaced holes 41 along the periphery. The holes 41 receive locking means such as bolts 42 that are adapted to be inserted therein at diametrically opposite positions, which bolts 42 are threaded into a pair of retaining means 43 each of which is slideably mounted in a guide bar 44 having a U-shape cross-section and exteding transversely across the table top sections 7, 8. The guide bars 44 are slideable in parallel longitudinally of the bench and are attachable, when desired, by means of locking means, not illustrated. The retaining means 43 in turn are adapted to be secured in a selected position in the guide bars 44 by means of e.g. a stop bolt 45. This arrangement thus provides for an adjustment and securing of the bar 34 at any angle relative the longitudinal direction of the bench and at any useful location on the surface of the table top sections 7, 8.

In accordance with a further aspect of this embodiment of the invention a limited and predetermined number of pad portions of strictly determined shape can be used for covering the surface of the table top sections 7, 8 surrounding the bar 34. On the circular disk 40 is placed, adjacent each side of the bar 34 a padding portion 24*a* having circularly curved peripheral edge (see FIGS. 8*a*–8*c*). To achieve a continuous padding surface, complementary padding portions 24*b* having a substantially semi-circular recess at complementary side edges for adaptation to the semi-circular pad portions 24*a*, and supplemental padding portions 24*c*, 24*d* and 24*e*, are then placed in position adjacent portions 24*a* and adjacent one another. Said supplemental padding portions are of modular construction not only to minimize the number of padding portions employed, but also to achieve all the required combinations that are further illustrated in FIGS. 8*a*–*e*. From said FIG. 8 it is thus evident that, by means of said padding portions, an almost freely selectable location of the position of the bar 34 can be achieved on the surface of the table top sections 7, 8 while still providing a continuous padding surface surrounding said bar.

As previously mentioned the freely movable journalling of at least one of the table top sections 7, 8 in the transverse direction makes it possible to examine, and when needed to treat the vertebral column of the patient in segments, i.e. vertebra for vertebra, to determine whether changes of the movability is present, namely restricted movability as well as movability in excess. To effect this type of examination, the patient is placed on the bench with the pair of vertebrae to be examined situated above the boundary line between the two table top sections 7, 8, and is secured thereto. By effecting a transverse motion of the table top sections relative to one another it can easily be determined whether there are changes in the movability between the pair of vertebrae being examined, and a treatment of said vertebrae can be carried out in a similar manner by suitable application of force.

We claim:

1. A traction bench for the treatment of the vertebral column and extremities of a human body comprising a table on which a patient to be treated may lie, said table comprising a pair of elongated separate table sections disposed in spaced longitudinally aligned relation to one another, support means attached to at least one of said table sections for mounting said one table section in a manner permitting said one table section to be displaced relative to the other of said table sections in any selected one or more of four different movements, said support means including first means supporting said one table section for translational movement longitudinally relative to said other table section along a first translational axis parallel to the longitudinal axis of said elongated one table section, second means supporting said one table section for translational movement transversely relative to said other table section along a second translational axis that is oriented at right angles to said first translational axis, third means supporting said one table section for tilting movement in a first angular direction relative to said other table section to tilt the plane of said one table section relative to the plane of said other table sections about a first pivotal axis which extends transversely to the direction of elongation of said one table section, and fourth means supporting said one table section for further tilting movement in a second angular direction transverse to said first angular direction to tilt the plane of said one table section transversely relative to the plane of said other table section about a second pivotal axis which extends parallel to the direction of elongation of said one table section, and fixation means on each of said table sections for fixedly securing one portion of the patient's body to one of said table sections and for fixedly securing another portion of the patient's body to the other of said table sections, said fixation means comprising a mounting structure which is adapted to be selectively moved to any one of a plurality of positions on the surface of its associated table section, means for securely attaching said mounting structure to the surface of said table section at the selected position on said surface, and a harness attached to said mounting structure for engagement with a portion of the patient's body adjacent said selected position on the surface of said table section, said mounting structure comprising a circular disc having an elongated bar extending across the diameter thereof, said disc being adapted to be attached to the selected position on the surface of said table section with said bar oriented in any selected one of a plurality of possible directions relative to the side edges of said table section, said harness being attached to said bar.

2. The traction bench of claim 1 including a plurality of modular pad sections adapted to be removably attached to the upper surface of said table section, the shapes and dimensions of said modular pad sections being selected to permit first ones of said pad sections to be disposed in overlying relation to portions of said circular disc in closely adjacent non-covering relation to said bar, and to permit other ones of said pad sections to be juxtaposed in closely adjacent relation to one another and to said first ones of said pad sections thereby to substantially completely cover at least those portions of said table section on which a patient's body lies.

3. A traction bench for the treatment of the vertebral column and extremities of a human body comprising a table on which a patient to be treated may lie, said table comprising a pair of elongated separate table sections disposed in spaced longitudinally aligned relation to one another, support means attached to at least one of said table sections for mounting said one table section for movement relative to the other of said table sections, said support means including first means supporting said one table section for free sliding translational motion longitudinally relative to said other table section along a first axis parallel to the direction of elongation of said one table section, and second means supporting said one table section for free sliding translational motion transversely relative to said other table section along a second axis that is transverse to the direction of elongation of said one table section, power means, and readily releasable coupling means for connecting said power means to said one table section to permit said power means to forcibly displace said one table section longitudinally toward and away from the other of said table sections along said first axis, said power means when so connected to said one tabel section restraining said one table section against transverse movement relative to said other table section along said second axis, said readily releasable coupling means being adapted to disconnect said power means from said one table section when desired thereby to permit said one table section to be freely movable in a transverse direction relative to said other table section along said second axis.

4. The traction bench of claim 3 wherein each of said table sections is mounted for longitudinal and transverse movements relative to the other of said table sections along said first and second axis respectively, said power means being connected by said readily releasable coupling means to each of said table sections individually.

5. The traction bench of claim 3 wherein said power means comprises a hydraulic cylinder, said readily releasable coupling means being disposed between said one of said table sections and the piston rod of said cylinder.

* * * * *